United States Patent [19]

Tedder

[11] 4,430,102
[45] Feb. 7, 1984

[54] FRACTIONAL DISTILLATION OF $C_2/C_3$ HYDROCARBONS AT OPTIMUM PRESSURES

[75] Inventor: Daniel W. Tedder, Marietta, Ga.

[73] Assignee: Georgia Tech Research Institute, Atlanta, Ga.

[21] Appl. No.: 438,935

[22] Filed: Nov. 3, 1982

Related U.S. Application Data

[63] Continuation of Ser. No. 299,623, Sep. 4, 1981, abandoned.

[51] Int. Cl.³ ............................................. F25J 3/02
[52] U.S. Cl. ...................................... 62/24; 208/351; 208/364
[58] Field of Search .............................. 62/21, 24–28; 208/351, DIG. 1, 364

[56] References Cited

U.S. PATENT DOCUMENTS 3,034,307  5/1962  Berger et al. ............................ 62/21

Primary Examiner—Frank Sever
Attorney, Agent, or Firm—Newton, Hopkins & Ormsby

[57] ABSTRACT

A method of recovering by distillation the separate components of a hydrocarbon gas mixture comprising ethylene, ethane, propylene and propane which comprises separating the ethylene as an overhead from an ethane, propylene and propane bottom in a first distillation tower at from about 500 to about 650 psia, separating ethane as an overhead from a propylene and propane bottom in a second distillation tower at from about 390 to about 520 psia, and separating propylene as an overhead from a propane bottom in a third distillation tower at from about 100 to about 170 psia is disclosed.

A mnethod of separating ethylene and ethane from propylene and propane in a first distillation tower at from about 400 to about 600 psia, separating the overhead product from the first tower in a second tower at from about 600 to about 700 psia to produce ethylene and ethane products, and separating a propylene/propane mixture in a third tower at from about 100 to about 170 psia is disclosed.

The heat for operating the propylene/propane splitter is derived from the cooling water of a heat exchange system or from hot quench tower oil.

1 Claim, 4 Drawing Figures

FRACTIONAL DISTILLATION OF $C_2/C_3$ HYDROCARBONS AT OPTIMUM PRESSURES

This is a continuation of application Ser. No. 299,623, filed Sept. 4, 1981 now abandoned.

BACKGROUND OF THE INVENTION

1. Field of the Invention

This invention relates to the fractional distillation of a $C_2/C_3$ hydrocarbon mixture into its component parts, i.e., ethane, ethylene, propane, propylene and is more particularly concerned with the optimizing of the expense of such fractional distillation.

2. Description of the Prior Art

It is well known that refinery off-gas or pyrolysis products of many saturated hydrocarbons offer a very large potential supply of olefinic hydrocarbons such as ethylene and propylene which do not otherwise occur naturally, and that these hydrocarbons are tremendously important as chemical intermediates. These hydrocarbons are useful not only for the manufacture of synthetic alcohols and rubber but also for the production of certain types of plastics and for many other purposes. However, ethylene and propylene are normally associated with other gases such as ethane and propane from which they can only be separated at considerable expense.

Illustrative of such a separation system is U.S. Pat. No. 2,645,104 wherein a $C_2/C_3$ feedstream, containing ethane, ethylene, propane and propylene is first separated by fractional distillation into an overhead stream (ethane and ethylene) and a bottoms stream (propane and propylene) and then each of these streams is separated into its components in respective second and third distillation towers.

The prior art relating to correlations which should be employed in arriving at the most economical manner of operating fractional distillation systems is that which was published by the applicant. There are: (1) D. W. Tedder, *The Heuristic Synthesis and Topology of Optimal Distillation Networks*, Ph.d These, Chemical Engineering, University of Wisconsin, Madison (August 1975); and (2) D. W. Tedder and D. F. Rudd, "Parametric Studies in Industrial Distillation: Part II Heuristic Optimization," *AIChE Journal* 24 (2) (March 1978) 323–334. However, these earlier correlations were based on bubble point feed temperatures only, and did not consider the effects of the overhead product mixture bubble point temperature and the bottoms product dew point temperature. These latter two quantities are highly important because they determine the feasible utility temperature (i.e., those of steam, refrigeration and cooling water.) Also, the earlier correlations are based on the normal feed mixture bubble point temperature (i.e., the bubble point estimated at 14.7 psia) rather than the present correlations wherein 485 psia is used as a pressure basis.

My earlier correlations do not predict the best operating pressures for mixtures of ethylene, ethane, propylene and propane. In fact many predictions using my earlier correlations are above the mixture critical point and, therefore, are not feasible.

The correlation of the present invention substantially improve on the earlier work because they predict that differences exist between towers 11, 14 and 15; and between towers 16 and 17; and between towers 18 and 19, discussed hereinafter. The earlier correlation would not predict that differences existed in these cases since it was based only on the feed bubble point. Also, the earlier correlations would predict only small differences existing between towers in the two sets (towers 11, 14, 15) and (towers 16, 17) and between towers 110 and 18, 19. As is pointed out hereinafter in Table 2, the correlations disclosed, here correctly predict that large differences do exist because of the effects of product compositions on the utility costs.

As shown in U.S. Pat. No. 2,500,353, a hydrocarbon feedstream may be subjected to serial removal of components, i.e., sequentially methane, ethylene, ethane, propylene, propane, etc. are removed from the feedstock in successive towers.

Various additional techniques are known in the distillation art for improving process economics or yields. Illustrative of such techniques are: U.S. Pat. No. 2,127,004—use of a single closed system refrigeration cycle to both reboil bottoms and condense overheads; U.S. Pat. No. 2,542,520—solvent extraction (extractive distillation); U.S. Pat. No. 2,577,617—propane absorber tower; U.S. Pat. No. 2,600,110—fractionator with refrigeration cycles; U.S. Pat. No. 2,722,113—fractional distillation of a partially condensed feedstream cooled by heat exchange with an expansion—cooled product stream; U.S. Pat. No. 2,952,983—avoidance of the formation of hydrocarbon hydrate; U.S. Pat. No. 3,119,677—recovery of hydrogen; U.S. Pat. No. 3,150,199—prevention of in-situ polymerization and by-product losses of desired components; and U.S. Pat. Nos. 3,359,743, 3,360,946, 4,140,504, 4,157,904 and 4,171,964—recovery of ethane and other components of natural gas.

A need therefore continues to exist for techniques whereby the process economics of such separations can be improved, particularly, with respect to utility costs which are a major cost burden on such processes.

SUMMARY OF THE INVENTION

Accordingly, one object of the invention is to provide a process for the separation of ethane, ethylene, propane and propylene at reduced cost.

Another object of the invention is to provide a process for the separation of ethane, ethylene, propane and propylene operating at optimum pressures which are substantially different from those currently contemplated in the art.

Another object of the invention is to operate the towers at the most economic pressures by avoiding the use of very cold refrigerants and exploiting favorable reductions in the species latent heats of vaporizataion.

Another object of the invention is to operate propylene/propane splitters at optimum pressures which permit the most economical use of cooling water as a heating medium.

Another object of the invention is to operate propylene/propane splitters at optimum pressures using as a heating medium either steam or hot quench tower oil, as is typically generated by ethylene quench towers.

Briefly, these object and other objects of the invention as hereinafter will become more readily apparent can be attained by providing a method of recovering by distillation the separate components of a hydrocarbon gas mixture containing ethane, ethylene, propane and propylene, the method comprising separating ethylene as an overhead product from an ethane, propane and propylene bottom in a first tower at from about 500 psia to about 650 psia, preferably, from about 550 psia to about 570 psia; separating ethane as an overhead product from a propane and propylene bottom in a second tower at from about 390 psia to about 520 psia, preferably, from about 410 psia to about 430 psia; and separating propylene as an overhead product from a propane bottom product in a third tower at about from 100 psia to about 170 psia, preferably, from about 120 psia to about 140 psia.

Also, the invention includes the method of separating an ethylene and ethane mixture from a propylene propane mixture in a tower operating at a pressure from about 400 to about 600 psia, but preferably at from about 470 to about 490 psia. The method of separating the ethylene ethane product from the first tower, in a second tower operating from about 600 to about 700 psia, but preferably at about 660 to about 680 psia.

BRIEF DESCRIPTION OF THE DRAWINGS

A more complete appreciation of the invention and many of the attentant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
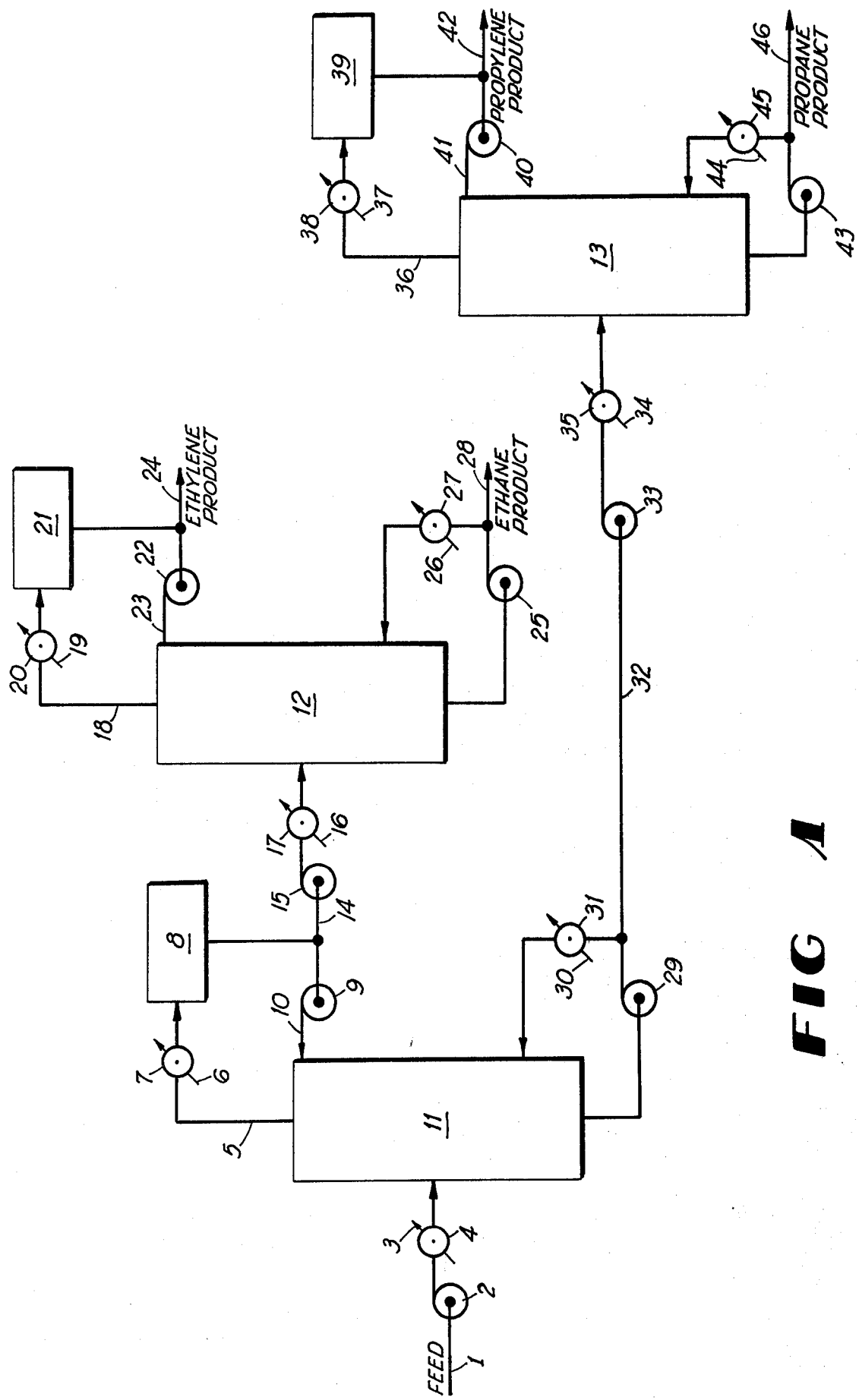
FIG. 1 is a schematic representation of a distillation sequence according to the present invention.

In commercial plants, the ethylene—and propylene—bearing fluid stream introduced into the recovery system contains various proportions of hydrogen, hydrocarbons and impurities such as carbon dioxide and nitrogen. The present invention relates only to that portion of the original stream fed which relates to the recovery system which contains essentially ethane, ethylene, propane and propylene, the remaining materials having been largely eliminated by processes conventional in the art.

In developing my system for predicting the optional deethanizer tower pressures which will result in the most economical recovery of the constitutents from the fluid stream, I derived certain empirical correlations. In arriving at this correlation ten different simple distillation towers, including those shown in FIGS. 1 and 2, were used to develop empirical correlations for predicting the optimal operating pressures for individual distillation towers that separate mixtures consisting primarily of ethylene, ethane, propylene and propane to commonly accepted specifications (i.e., to ethylene and propylene product specifications and to ethane and propane recycle specifications).

The correlations are based on the data that are summarized below on Table A where the "A" designation refers to ethylene, "B" refers to ethane, "C" refers to the propylene species and "D" refers to propane. Table A is believed to be valuable in itself, for predicting optimal tower operating pressures for feeds with different compositions from that which are disclosed herein.

The following constraints are applicable:

1. The correlation assumes cooling water is used only according to common practice.
2. Reboiler heat is supplied using steam according to common practice.
3. Refrigeration is available according to common practice.
4. Each tower receives only a single feed and produces two product effluents.

In order to use the correlation, it is necessary to calculate three immportant temperatures that mathematically embody the effect of pressure on operating costs and capital investment requirements. These temperatures are all evaluated using standard bubble point and dew point temperature estimation procedures, but at 485 psia pressures for each mixture that is considered. The optimal tower operating pressure, P* in psia, is thus determined by the equation:

$$\log_e (P^*) = 2.677 - \frac{309.4}{T_{FB}} + \frac{1147.6}{T_{\phi B}} + \frac{1087.4}{T_{BD}}$$

where:

$T_{FB}$ = tower feed mixture bubble point temperature (° R) evaluated at 485 psia $T_{\phi B}$ = tower overhead product mixture bubble point temperature (° R) evaluated at 485 psia $T_{BD}$ = tower bottom product mixture dew point temperature (° R) evaluated at 485 psia.

The correlation fits the observations in Table A with a standard deviation of ±15.3 psia i.e., between about 290 psia and about 680 psia. The observed and predicted optimal pressure deviations are presented in Table B. The nonlinear parameter confidence intervals for the parameters indicate that all parameters are statistically significant.

TABLE A

Data base for empirical pressure correlation

| Tower | | Temperatures (°F.) | | | OPTIMAL PRESSURE |
|---|---|---|---|---|---|
| Number | Split | $T_{FB}$ | $T_{\phi B}$ | $T_{BD}$ | (PSIA) |
| 11 | AB/CD | 48.67 | 25.47 | 168.74 | 450.0 |
| 12 | A/B | 25.47 | 18.55 | 65.85 | 669.3 |
| 13 | C/D | 167.89 | 167.06 | 182.94 | 291.3[a] |
| 14 | A/BCD | 48.67 | 18.55 | 137.43 | 544.3 |
| 15 | ABC/D | 48.67 | 47.32 | 182.94 | 410.2 |
| 16 | A/BC | 47.33 | 18.55 | 135.42 | 538.9 |
| 17 | AB/C | 47.33 | 25.46 | 167.86 | 496.7 |
| 18 | B/CD | 121.05 | 62.28 | 168.75 | 431.6 |
| 19 | BC/D | 121.05 | 118.96 | 182.93 | 350.2 |
| 110 | B/C | 118.96 | 62.28 | 167.87 | 435.9 |

[a]Optimal conditions using 10 lb steam, near optimal using hot quench liquid.

TABLE B

Observed and predicted optimal pressures and residuals.

| Tower | | Optimal Pressures (PSIA) | | |
|---|---|---|---|---|
| Number | Split | Observed | Calculated | Residual |
| 11 | AB/CD | 450.0 | 475.4 | 25.4 |
| 12 | A/B | 669.3 | 670.5 | 1.2 |
| 13 | C/D[a] | 291.3 | 301.0 | 9.7 |
| 14 | A/BCD | 544.3 | 538.7 | −5.6 |
| 15 | ABC/D | 410.2 | 413.2 | 3.0 |
| 16 | A/BC | 538.9 | 541.1 | 2.2 |
| 17 | AB/C | 496.7 | 475.8 | −20.9 |
| 18 | B/CD | 431.6 | 434.0 | 2.4 |
| 19 | BC/D | 350.2 | 336.8 | −13.4 |
| 110 | B/C | 435.9 | 434.3 | −1.6 |
| STANDARD DEVIATION = ± 15.3 psia | | | | |

[a]Optimal condition using 10 lb steam, near optimal using hot quench liquid.

Referring now to the drawings, as illustrated in FIG. 1, the feed stream 1, containing primarily ethane, ethylene, propane and propylene, is passed through pump 2 and heat exchanger 4 into a first distillation tower 11, which is typically a sieve or bubble-cap tray fractionating column. The vaporous overhead 5 is condensed in condenser 7 with the condensate accumulated in pressure vessel 8, a part being returned as reflux through pump 9 and line 10 and the balance being removed through line 14. The first tower 11 in this embodiment is operated at from about 400 psia to about 600 psia, preferably, from about 460 psia to about 480 psia, so as to produce an overhead in line 14 containing only ethane and ethylene.

This $C_2$ fraction is then passed through pump 15 and heat exchanger 17 into a second distillation tower 12, which is also conveniently of the sieve tray type. The gaseous overhead 18 is condensed in condenser 20 with the condensate accumulated in pressure vessel 21, a part being returned as reflux through pump 22 and line 23 and ethylene is removed through line 24. A reboiled circuit including pump 25 and heat exchanger 27 is used at the bottom and ethane is removed through line 28. The second tower 12 is operated at from about 600 psia to about 700 psia, preferably, from about 660 psia to about 680 psia.

The first tower 11 is also provided with a reboiler circuit including pump 29 and heat exchanger 31. The bottoms removed through line 32 containing propane and propylene. This bottoms stream is passed through pump 33 and heat exchanger 35 into a third distillation tower 13, which is also conveniently of the sieve tray type. The gaseous overhead 36 is condensed in condenser 38 with the condensate accumulated in pressure vessel 39, a part being returned as reflux through pump 40 and line 41 and propylene removed through line 42. A reboiler circuit including pump 43 and heat exchanger 45 is used at the bottom and propane is removed through line 46. The third tower 113 is operated at between about 100 psia and about 170 psia, preferably, from between about 120 and about 140 psia.

Figure 2:
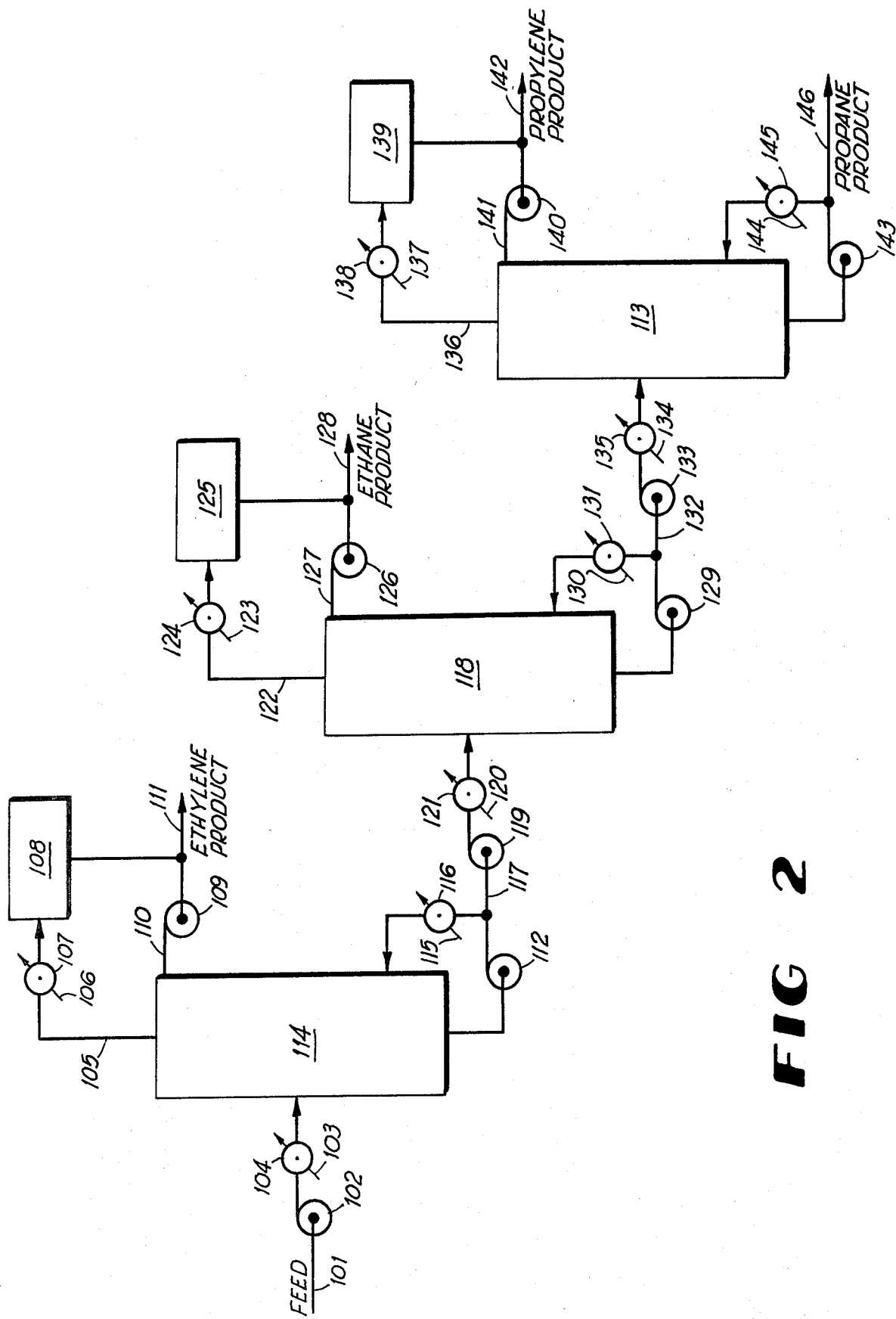
FIG. 2 is a schematic representation of an alternative distillation sequence according to the present invention.

In accordance with a preferred embodiment of the invention, as illustrated in FIG. 2, the distillation sequence of the process is altered. As shown in FIG. 2, the feed stream 101, containing primarily ethane, ethylene, propane and propylene, is passed through pump 102 and heat exchanger 104 into a first tower 114, which is typically a sieve tray fractionating column. The gaseous overhead 105 is condensed in condenser 107 with the condensate accumulated in pressure vessel 103, a part being returned as reflux through pump 109 and line 110 and ethylene being removed through line 111. The first distillation tower 14 is operated at a pressure of from about 500 psia to about 650 psia, preferably, from about 550 to about 570 psia.

The first tower 114 is also provided with a reboiler circuit including pump 112 and heat exchanger 116. The bottoms removed through line 117 containing ethane, propane and propylene. This bottom stream is passed through pump 119 and heat exchanger 121 into a second distillation tower 118, which is also conveniently of the sieve tray type. The gaseous overhead 122 is condensed in condenser 124 with the condensate accumulated in pressure vessel 125, a part being returned as reflux through pump 126 and line 127 and ethane removed through line 128. The second tower 18 is operated at a pressure of from about 390 psia to about 520 psia, preferably from about 410 psia to about 430 psia.

The second tower 18 is also provided with a reboiler circuit including pump 129 and heat exchanger 131. The bottoms removed through line 132 containing propane and propylene. This bottom stream is passed through pump 133 and heat exchanger 135 into a third tower 113, which is also conveniently of the sieve tray type. The gaseous overhead 136 is condensed in condenser 138 with the condensate accumulated in pressure vessel 139, a part being returned as reflux through pump 140 and line 141 and propylene removed through line 142. The third tower 113 is operated at a pressure of from about 100 psia to about 170 psia, preferably at from about 120 psia to about 140 psia.

The third distillation tower 113 is also provided with a reboiler circuit including pump 143 and heat exchanger 145 and propane is removed through line 146.

As noted in the above discussion, the operational pressures of the distillation columns 11 and 12, according to the present invention, are substantially different from those normally contemplated by the art. As a benchmark for purposes of comparison, a current commercial process utilizing the configuration of FIG. 1 utilizes pressures of about 350 psia in tower 11, about 300 psia in tower 12 and about 250 psia in tower 13. Such operating pressures are generally arrived at by consideration of the relative volatility of the components to be separated, i.e., the degree of separation attainable at a given pressure, along with certain cost factors such as tower size and available utilities.

In particular, for towers 11 and 12, it is well known that the relative volatilities of the species separated decrease with increasing tower pressures. This simple observation by itself suggests that the minimum vapor requirements increase with increasing pressures. Consequently, these tower condenser and reboiler duties have also been assumed to invariably increase with pressure according to the common belief of those skilled in the art. Therefore, common practice has been to operate towers 11 and 12 of the sequence in FIG. 1 at pressures which are substantially below the economically favored conditions.

In addition, it has been common practice to operate towers 11 and 12 at substantially less than economic pressures due to concerns for hydraulic instabilities. However, because of significant improvements in on-line process control in recent years, these stability concerns are not detrimental to the overall value of the invention. On the other hand, stability considerations enhance the value of the sequence in FIG. 2, relative to the configuration that is shown as FIG. 1, i.e., towers 14 and 18.

Also, it has been common practice to operate towers 12 and 13 at pressures that are substantially different from the optimal conditions in order to permit heat transfer from the tower 13 condenser to the tower 12 reboiler. This practice mistakenly assumes that heat exchanger matching between these two towers is valuable. However, I have found that the most important economic considerations are the condenser costs for tower 12 and the reboiler costs for tower 13 which are adversely affected by this current practice of optimization. On the other hand, my invention reduces the costs of these latter two quantities substantially.

I have discovered that significantly different operating pressures result in substantial process economies, primarily with respect to the cooling requirements of reflux condensers and feed heat exchangers, with only moderate increases in the capital expenditures necessary to achieve desirable separation. Also, my invention permits a novel use of cooling water to supply reboiler heat to propylene/propane towers. Alternatively, my invention permits the optimum use of reboiler steam or hot quench oil. Moreover, in a preferred embodiment, favorable synergisms between the distillation sequence and the tower operating pressures have been discovered that substantially reduce the system utility requirements. Illustrative of the favorable results obtainable at higher pressures, is the effect of operating pressure on the ethane/propylene splitter (tower 11, FIG. 1) as shown in Table 1.

TABLE I

| Pressure (psia) | Overhead Temp. (°F.) | Relative Volatility | Minimum Vapor rate (lb-moles/hr) | Feed & Reflux Condenser Duties ($10^6$ BTU/hr.) | Latent Heat of Vaporization (BTU lb-mole) |
|---|---|---|---|---|---|
| 200 | −29.4 | 3.751 | 5348 | 38.73 | 4366.7 |
| 250 | −15.8 | 3.405 | 5563 | 38.39 | 4096.7 |
| 300 | −4.2 | 3.133 | 5730 | 37.16 | 3844.4 |
| 350 | 5.9 | 2.907 | 5954 | 34.24 | 3590.8 |
| 400 | 15.0 | 2.714 | 6192 | 31.25 | 3346.1 |
| 450 | 23.1 | 2.543 | 6452 | 26.99 | 3082.7 | a—Temperature of the overhead vapor.
b—Ethane/propylene relative volatility evaluated at the overhead vapor temperature.
c—The pinch point for the tower is located below the feed tray.
d—Latent heat is for the overhead product of tower 11, as set forth in Table 2.

As may be readily ascertained, the relative volatility, of course, decreases with increasing pressure. This change also increases the minimum vapor requirements for higher pressures, but the overall condenser duties decrease. This latter result occurs because of reduced latent heats of vaporization at the higher pressures. These results are set forth for the tower 11 overheads (FIG. 1) as shown in Table 2, however, similar trends are observed for all columns.

TABLE 2

OVERALL MATERIAL FLOWRATES FOR DISTILLATION SEQUENCE OF FIG. 1

| Feed | Tower 11 | | Tower 12 | | Tower 13 | |
|---|---|---|---|---|---|---|
| | Overheads | Bottoms | Ethylene Product | Ethane Product | Propylene Product | Propane Product |
| Ethylene | 3180. | 3179.84 | 0.16 | 3179. | 0.84 | 0.159 | 0.001 |
| Ethane | 670. | 669.52 | 0.48 | 1.24 | 668.25 | 0.472 | 0.004 |
| Propylene | 1053. | 12. | 1041. | 0.12 | 11.88 | 1039.9 | 1.1 |
| Propane | 85. | 8. | 77. | 0.08 | 7.92 | 9.5 | 67.5 |

The surprising thing is the fact that although the minimum vapor requirements increase with pressure, the latent heat of vaporization decreases with pressure with a net effect that the heat of condensation decreases with increasing pressure for those towers 11, 12, 13, 113 and 118. With a propylene/propane splitter this is not so. In other words, the minimum vapor requirements increase faster than the latent heat of vaporization decreases. Therefore with that tower the relative volatility decreases to force operation at the lower pressure with the hot oil quencher around 290 psia and with the cooling water around 130 psia. For every different mixture there are different conditions.

The nominal product specification used in Table 2 are:

Ethylene product: <0.05% ethane
Ethane product: <0.15% ethylene
Propylene product: ≦1% propane
Propane product: ≦2% propylene.

Moreover, in addition to the reduced latent heat of vaporization, the overhead temperature increases, thus, allowing the use of less costly coolant streams, (i.e., higher temperature coolant streams).

Figure 4:
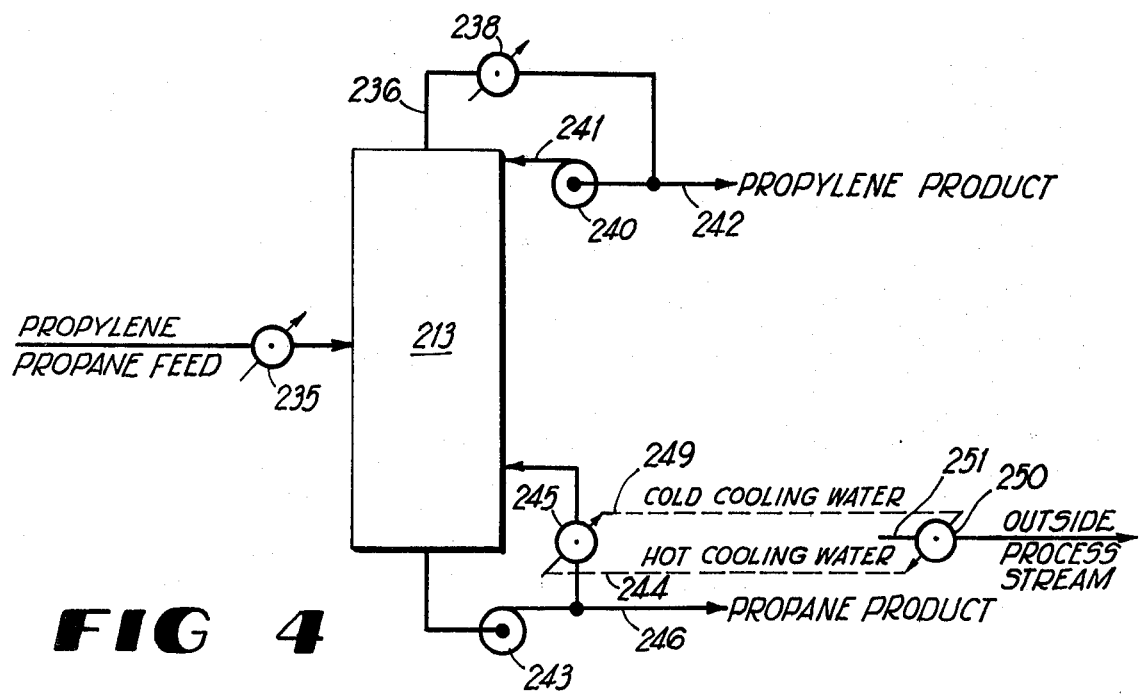
FIG. 4 is a schematic representation of another alternate propylene/propane tower utilities optimization method according to the present invention.

In FIG. 4 a tower 213 which is similar to the third tower 13. Propylene/propane gas is fed through heat exchanger 235 into the tower 213 and the gaseous overhead 236 is condensed in condenser 238 and the condensate discharge through line 242. A part of the propylene is returned via pump 240 and line 241 to the tower 213. As illustrated in Table 13, hereinafter, the tower of FIG. 4 is operated at a pressure of between about 100 psia to about 170 psia and preferably at 130 psia. Under such conditions, hot cooling water from a conventional cooling system can be used for providing heat for a reboiler circuit which includes pump 243 and heat exchanger 245. Propane is discharged through line 246. The hot cooling water is supplied from a heat exchanger 250 via line 244 and returned thereto as cold cooling water via line 249. This heat exchanger also has an outside process stream via line 251. The efficiency of the system of FIG. 4 is demonstrated in Table 13 hereof.

Figure 3:
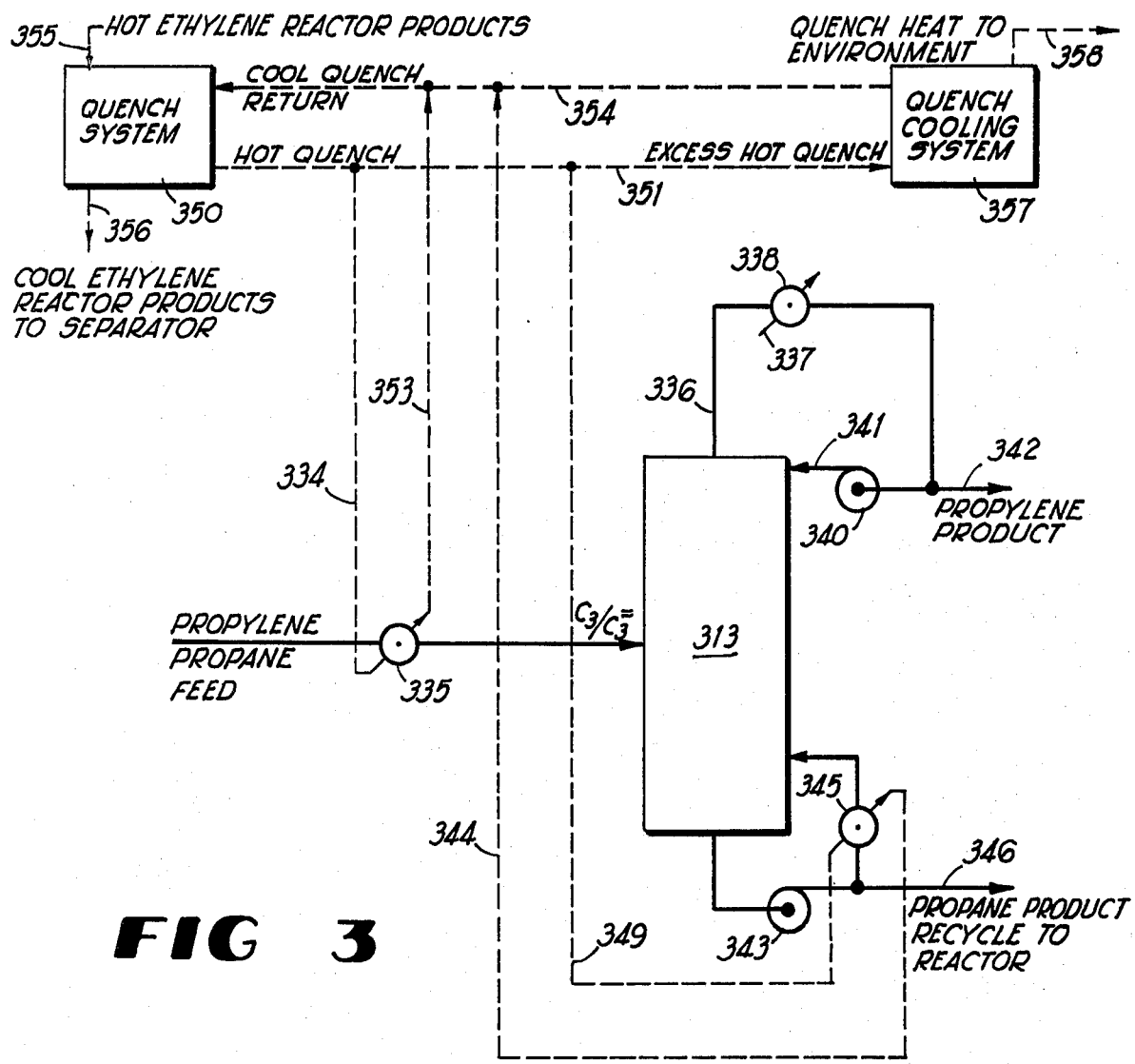
FIG. 3 is a schematic representation of one method of optimizing a propylene/propane tower utilities according to the present invention.

In FIG. 3, the third tower 313 is illustrated as receiving a propylene/propane feed from a second tower (not shown). This propane and propylene is fed through a heat exchanger 335 into tower 313, which also has sieve trays. The gaseous overhead 336 is condensed in condenser 338 with a portion of the condensate being returned via pump 340 to the tower 313. The propylene product is discharged via line 342.

This third tower 313 is operated at a pressure of from about 250 psia to about 300 psia and preferably at approximately 290 psia. This third tower 313 is also provided with a reboiler circuit including pump 343 and heat exchanger 345, the propane being removed through line 346.

In the present embodiment, the two heat exchangers 335 and 345 are provided with heat via lines 334 and 344, respectively, the heat medium being liquid from a hot quench line 351. Lines 353 and 349, respectively return the heating liquid or medium from the heat exchangers 335 and 345 respectively to the cold quench return line 354.

It will be understood by those skilled in the art that hot ethylene reactor products are fed through a heat exchanger 350 via a line 355 and discharged therefrom via line 356 as cool ethylene reactor products to a separator. The hot quench fluid passes from the heat exchanger 350 along line 351 to a quench cooling system 357 and is returned to the quench system 350 via line 354. The quench cooling system discharges the excess quench heat to the environment via line 358.

Table 16 illustrates the efficiency of the system of Table 16.

Having generally described this invention, a further understanding can be obtained by reference to certain specific examples which are provided herein for purposes of illustration only and are not intended to be limiting unless otherwise specified.

In all the examples which follow, the capital investment requirements are based upon short-cut design methods consisting of a modified Fenske-Underwood-Gilliland technique and the cost correlations developed by Guthrie ("Data and Techniques for Preliminary Capital Cost Estimating", *Chem. Eng.* (Mar. 24, 1969) p. 114). These costs have been factored to mid-1979 using the M & S equipment cost index (a factor of 2.2.)

Equilibrium K values were estimated using the Chao-Sender calculational method and verified from experimental data published in the literature. Latent heats or vaporization were estimated from the Watson correlation. The design methodology considers changes in molar flowrates at different points in the towers and, therefore, the effects of latent and sensible heat changes.

The annual utility costs were calculated from the assumed operating schedule of 8500 hrs/yr., the estimated utility requirements for the process, and the utility cost schedule that is shown in Table 3 (based on typical on-site costs). Additional equipment specifications that are used in determining tower heights and equipment costs are set forth in Table 4.

TABLE 3

| Utility | Available T$^a$ | Cost$^{b,c}$ |
|---|---|---|
| Cooling Water | 75 | 0.15 |
| Propylene | 40 | 2.86 |
| Refrigerant | 0 | 7.51 |
|  | −40 | 11.19 |
| Ethylene | −75 | 13.97 |
| Refrigerant | −110 | 18.35 |
|  | −140 | 23.04 |
| Steam | 239 | 6.63 |

$^a$All temperatures in °F.
$^b$Costs have been truncated to the nearest cent.
$^c$All costs in dollars per million BTU's transferred.

TABLE 4

| Tower | = | Carbon-Steel vertical pressure vessel with sieve trays spaced at 1.5 ft. |
|---|---|---|
| Reflux Condenser Reboiler Feed Heat Exchanger | = | Carbon-steel shell-and-tube exchangers |
| Feed Pump Reboiler Pump Reflux Pump | = | Carbon-steel centrifugal pumps and drivers |
| Reflux Drum | = | Carbon-steel horizontal pressure vessel with the length equal to 2 times the diameter. Nominal space time is 7.5 minutes. |

COMPARATIVE EXAMPLE 1

In accordance with FIG. 1, a separation process was run in accordance with conventional procedures to obtain the separation set forth in Table 2, above. A summary of the process operating conditions is set forth in Table 5. Equipment specification for the various towers are set forth in Tables 6, 7 and 8. The results are set forth in Tables 17, 18A and 19.

TABLE 5

| Tower | Split$^a$ | Tray | P (psia) | T$^b$ (°F.) | Rates (1$^b$ - moles/hr) Vapor | Rates (1$^b$ - moles/hr) Liquid | Utilities (10$^6$ BTU/hr) Reflux Condenser | Utilities (10$^6$ BTU/hr) Feed Heat Exch. | Utilities (10$^6$ BTU/hr) Reboiler |
|---|---|---|---|---|---|---|---|---|---|
| 11 | AB/CD | Top | 350.0 | 2.5 | 7707 | 3838 | −27.7 | | |
| 69 Actual Trays | | Feed | 352.0 | 32.2 | 6190 | 2320 | | 0.5 | |
| | | Bottom | 354.0 | 140.6 | 4510 | 5628 | | | 20.4 |
| 12 | A/B | Top | 300.0 | −14.1 | 11902 | 8722 | −44.6 | | |
| 140 Actual Trays | | Feed | 302. | −7.5 | 11516 | 8336 | | 3.2 | |
| | | Bottom | 304. | 27.8 | 9876 | 10565 | | | 40.2 |
| 13 | C/D | Top | 250.0 | 111.3 | 8852 | 7802 | −46.7 | | |
| 291 Actual Trays | | Feed | 252. | 112.3 | 8858 | 7808 | | 0.1 | |
| | | Bottom | 254. | 126.6 | 8445 | 8514 | | | 44.2 |

$^a$A = Ethylene B = Ethane C = Propylene D = Propane
$^b$Temperature of the bubble point liquid overflow.

TABLE 6 tower 11

| Item | Description | Capital Investment ($1000) | Annual Utility Cost ($1000) |
|---|---|---|---|
| Tower | 69 Actual Trays 8.6 Ft. Diam., 114 Ft. High | 743 | |
| Reflux Condenser | 27.7 MBTU/hr, 6270 Ft$^2$ (−40° Propylene) | 303 | 2,632 |
| Reflux Drum | 6837 gallons | 57 | |
| Reboiler | 20.5 MBTU/hr, 2072 Ft$^2$ 239° Steam | 148 | 974 |
| Feed Heat Exchanger | 0.5 MBTU/hr, 98 Ft$^2$ 239 steam | 20 | 27 |
| Reflux Pump | 14.8 BHP, 454 GPM | 11 | 3 |
| Reboiler Pump | 5.1 BHP, 740 GPM | 5 | 1 |
| | TOTALS | 1,287 | 3,637 |

TABLE 7 tower 12

| Item | Description | Capital Investment ($1000) | Annual Utility Cost ($1000) |
|---|---|---|---|
| Tower | 140 Actual Trays 11. Ft. Diam., 220 Ft. High | 1,460 | |
| Reflux Condenser | 44.6 MBTU/hr, 17,231 Ft$^2$ (−40° Propylene) | 560 | 4,242 |
| Reflux Drum | 10,214 gallons | 71 | |
| Reboiler | 40.2 MBTU/hr, 6682 Ft$^2$ (Matched with Tower 13) | 304 | |
| Feed Heat Exchanger | 3.2 MBTU/hr, 353 Ft$^2$ (−40° propylene) | 45 | 182 |

TABLE 7-continued tower 12

| Item | Description | Capital Investment ($1000) | Annual Utility Cost ($1000) |
|---|---|---|---|
| Reflux Pump | 48 BHP, 998 | 24 | 10 |
| Reboiler Pump | 5 BHP, 1307 GPM | 6 | 1 |
| | TOTALS | 2,166 | 4,435 |

TABLE 8 tower 13 and 113

| Item | Description | Capital Investment ($1000) | Annual Utility Cost ($1000) |
|---|---|---|---|
| Tower | 291 Actual Trays 11.5 Ft. Diam., 446 Ft. high | 2,188 | |
| Reflux Condenser | 46.7 MBTU/Hr, 1080 Ft$^2$ (matched with tower 12, excess with cooling water) | 102 | 8 |
| Reflux Drum | 10,681 gallons | 70 | |
| Reboiler | 44.2 MBTU/hr, 3917 Ft$^2$ (239° F. steam) | 205 | 2,102 |
| Feed Heat Exchanger | 0.1 MBTU/hr, 14 Ft$^2$ (239° F. steam) | 5 | 7 |
| Reflux Pump | 114 BHP, 1255 GPM | 41 | 23 |
| Reboiler Pump | 5 BHP, 1455 GPM | 6 | 1 |
| | TOTALS | 2,617 | 2,141 |

EXAMPLE 1

In accordance with FIGS. 1 and 4, a separation process was run in accordance with this invention to obtain the separation set forth in Table 2, above. A summary of the process operating conditions is set forth in Table 9. Equipment specifications for the various towers are set forth in Tables 10, 11 and 12. The results are set forth in Tables 17, 18A and 19.

TABLE 9

| Tower | Split$^a$ | Tray | P (psia) | T$^b$ (°F.) | Rates (1$^b$ - moles/hr) Vapor | Rates (1$^b$ - moles/hr) Liquid | Utilities (10$^6$ BTU/hr) Reflux Condenser | Utilities (10$^6$ BTU/hr) Feed Heat Exch. | Utilities (10$^6$ BTU/hr) Reboiler |
|---|---|---|---|---|---|---|---|---|---|
| 11 | AB/CD | Top | 450.0 | 20.0 | 7835 | 3966 | −24.1 | | |
| 63 Actual Trays | | Feed | 452.0 | 51.62 | 6908 | 3039 | | 3.9 | |
| | | Bottom | 454.0 | 162.0 | 4575 | 5693 | | | 17.4 |
| 12 | A/B | Top | 669.0 | 42.2 | 10039 | 6858 | −16.8 | | |
| 227 Actual Trays | | Feed | 671. | 49.9 | 20309 | 17128 | | 9.5 | |
| | | Bottom | 673. | 88.6 | 11786 | 12475 | | | 13.2 |
| 13 | C/D | Top | 123.0 | 59.6 | 7302 | 6252 | −46.1 | | |
| 229 Actual Trays | | Feed | 125. | 61.6 | 7303 | 6253 | | −0.005 | |
| | | Bottom | 127. | 74.6 | 6382 | 6450 | | | 40.4 |

$^a$A = Ethylene B = Ethane C = Propylene D = Propane
$^b$Temperature of the bubble point liquid overflow.

TABLE 10 tower 11

| Item | Description | Capital Investment ($1000) | Annual Utility Cost ($1000) |
|---|---|---|---|
| Tower | 63 Actual Trays 8.2 Ft. Diam., 104 Ft. high | 699 | |
| Reflux Condenser | 24.1 MBTU/Hr, 11,200 Ft$^2$ (0° propylene) | 478 | 1,540 |
| Reflux | 7035 gallons | 63 | |

TABLE 10-continued tower 11

| Item | Description | Capital Investment ($1000) | Annual Utility Cost ($1000) |
|---|---|---|---|
| Drum | | | |
| Reboiler | 17.4 MBTU/hr, 2251 Ft$^2$ (239° F. steam) | 169 | 827 |
| Feed Heat Exchanger | 3.9 MBTU/hr, 927 Ft$^2$ (cooling water to heat feed) | 95 | 5 |
| Reflux Pump | 14 BHP, 475 GPM | 10 | 3 |
| Reboiler Pump | 5 BHP, 759 GPM | 5 | 1 |
| | TOTALS | 1,519 | 2,376 |

TABLE 11 tower 12

| Item | Description | Capital Investment ($1000) | Annual Utility Cost ($1000) |
|---|---|---|---|
| Tower | 227 Actual Trays 11.7 Ft. Diam., 350 Ft. high | 2,555 | |
| Reflux Condenser | 16.8 MBTU/Hr, 3990 Ft$^2$ (0° propylene) | 286 | 1,074 |
| Reflux Drum | 8957 gallons | 85 | |
| Reboiler | 13.2 MBTU/hr, 16092 Ft$^2$ (cooling water to heat) | 710 | 76 |
| Feed Heat Exchanger | 9.5 MBTU/hr, 1836 Ft$^2$ (cooling water to heat) | 173 | 12 |
| Reflux Pump | 58 BHP, 816 GPM | 27 | 12 |
| Reboiler Pump | 6 BHP, 1621 GPM | 6 | 1 |
| Feed Pump | 93 BHP, 473 GPM | 36 | 19 |
| | TOTALS | 3,878 | 1,194 |

TABLE 12 tower 213

| Item | Description | Capital Investment ($1000) | Annual Utility Cost ($1000) |
|---|---|---|---|
| Tower | 229 Actual Trays 12.4 Ft. Diam., 353 Ft. high | 1,905 | |
| Reflux Condenser | 46.1 MBTU/Hr, 23,408 Ft$^2$ (40° F. propylene) | 594 | 1,120 |
| Reflux Drum | 8,561 gallons | 55 | |
| Reboiler | 40.4 MBTU/hr, 28,323 Ft$^2$ (cooling water for heat) | 673 | 56 |
| Feed Heat Exchanger | 0.005 MBTU/hr, 1 Ft$^2$ (40° F. Propylene) | 0.8 | 0.1 |
| Reflux Pump | 76 BHP, 977 GPM | 32 | 15 |

TABLE 12-continued tower 213

| Item | Description | Capital Investment ($1000) | Annual Utility Cost ($1000) |
|---|---|---|---|
| Reboiler Pump | 5 BHP, 1069 GPM | 6 | 1 |
| | TOTALS | 3,266 | 1,192 |

EXAMPLE 2

In accordance with FIG. 2, a separation process was run, in accordance with this invention, to obtain product streams as defined in Table 2, above. A summary of the process operating conditions is set forth in Table 13. Equipment specifications for the various towers are set forth in Tables 14, 15 and 16. The results are set forth in Tables 17, 18A and 19.

TABLE 13

| Tower | Split[a] | Tray | P (psia) | T[b] (°F.) | Rates ($1^b$ - moles/hr) Vapor | Rates ($1^b$ - moles/hr) Liquid | Utilities ($10^6$ BTU/hr) Reflux Condenser | Utilities ($10^6$ BTU/hr) Feed Heat Exch. | Utilities ($10^6$ BTU/hr) Reboiler |
|---|---|---|---|---|---|---|---|---|---|
| 14 | AB/CD | Top | 517.0 | 23. | 13489 | 10309 | −36.3 | | |
| 209 Actual Trays | | Feed | 519.0 | 50. | 15906 | 12725 | | −0.1 | |
| | | Bottom | 521.0 | 127. | 10837 | 12644 | | | 35.9 |
| 18 | A/B | Top | 432.0 | 53. | 3203 | 2514. | −10.7 | | |
| 74 Actual Trays | | Feed | 434. | 114. | 2679 | 1990 | | −0.2 | |
| | | Bottom | 436. | 158. | 2329 | 3447 | | | 9.2 |
| 13 | C/D | Top | 123.0 | 60. | 7302 | 6252 | −46.1 | | |
| 229 Actual Trays | | Feed | 125. | 62. | 7303 | 6253 | | −0.005 | |
| | | Bottom | 127. | 75. | 6382 | 6450 | | | 40.4 |

TABLE 14 tower 114

| Item | Description | Capital Investment ($1000) | Annual Utility Cost ($1000) |
|---|---|---|---|
| Tower | 204 Actual Trays 12.5 Ft. Diam., 315 Ft. high | 2,373 | |
| Reflux Condenser | 36.3 MBTU/Hr, 15,704 Ft² (0° propylene) | 627 | 2,316 |
| Reflux Drum | 11,880 gallons | 92 | |
| Reboiler | 35.9 MBTU/hr, 3453 Ft² (239° F. steam) | 235 | 1,707 |
| Feed Heat Exchanger | 0.1 MBTU/hr, 28 Ft² (0° F. Propylene) | 10 | 9 |
| Reflux Pump | 75 BHP, 1211 GPM | 32 | 15 |
| Reboiler Pump | 6 BHP, 1675 GPM | 7 | 1 |
| Feed Pump | 44 BHP, 641 GPM | 22 | 9 |
| | TOTALS | 3,398 | 4,057 |

TABLE 15 tower 118

| Item | Description | Capital Investment ($1000) | Annual Utility Cost ($1000) |
|---|---|---|---|
| Tower | 74 Actual Trays 5.5 Ft. Diam., 120 Ft. high | 501 | |
| Reflux Condenser | 10.7 MBTU/Hr, 7203 Ft² (40° propylene) | 354 | 261 |
| Reflux Drum | 3,232 gallons | 43 | |
| Reboiler | 9.2 MBTU/hr, 1135 Ft² (239° F. steam) | 107 | 437 |

TABLE 15-continued tower 118

| Item | Description | Capital Investment ($1000) | Annual Utility Cost ($1000) |
|---|---|---|---|
| Feed Heat Exchanger | 0.2 MBTU/hr, 20 Ft² (40° F. Propylene) | 8 | 4 |
| Reflux Pump | 12 BHP, 338 GPM | 9 | 2 |
| Reboiler Pump | 6 BHP, 386 GPM | 5 | 1 |
| | TOTALS | 1,027 | 705 |

TABLE 16 tower 313
Tower 13 (using 190° F. Hot Water)
Tower Pressure = 290 psia

| Item | Description | Capital Investment ($1000) | Annual Utility Cost ($1000) |
|---|---|---|---|
| Tower | 299 Actual Trays 11.5 Ft. Diam., 458 Ft. high | 2,272 | |
| Reflux Condenser | 47.2 MBTU/Hr, 34,686 Ft² (cooling water) | 876 | 73 |
| Reflux Drum | 11,511 gallons | 76 | |
| Reboiler | 44.9 MBTU/hr, 4475 Ft² (190° F. hot water) | 232 | 57 |
| Feed Heat Exchanger | 0.2 MBTU/hr, 18 Ft² (190° F. hot water) | 6 | 0.3 |
| Reflux Pump | 125 BHP, 1365 GPM | 44 | 25 |
| Reboiler Pump | 6 BHP, 1589 GPM | 7 | 1 |
| | TOTALS | 3,513 | 156 |

VC = 1135

Table 17 summarizes the utility requirements, based on the operating parameters of Tables 5, 9 and 13, for each of the columns in the Examples. Available utilities were propylene refrigerant (−40, 0 and 40° F.), cooling water (75° F.) and hot water (190° F.). Utility selection was based on a design criteria of a minimum 7.5° F. temperature differential across the heat transfer surface. As may be readily ascertained, operation at optimal pressures (Example 1) or at optimal pressures with a modified distillation sequence (Example 2) allows the use of less expensive utilities, (i.e., less refrigeration is needed and cooling water may be used economically as a heating medium).

TABLE 17

| | Tower | Split | Utility Temperature[a,b] (°F.) Reflux | Utility Temperature[a,b] (°F.) Feed | Utility Temperature[a,b] (°F.) Reboiler |
|---|---|---|---|---|---|
| Comp. Ex. 1 | 11 | AB/CD | −40 | 239 | 239 |
| | 12 | A/B | −40 | −40 | Matched |

TABLE 17-continued

| | Tower | Split | Utility Temperature[a,b] (°F.) | | |
|---|---|---|---|---|---|
| | | | Reflux | Feed | Reboiler |
| | 13 | C/D | Matched | 239 | 190 |
| Ex. 1 | 11 | AB/CD | 0 | 100 | 239 |
| | 12 | A/B | 0 | 100 | 100 |
| | 13 | C/D | 40 | 40 | 100 |
| Ex. 2 | 14 | A/BCD | 0 | 0 | 239 |
| | 18 | B/CD | 40 | 40 | 239 |
| | 13 | C/D | 40 | 40 | 100 |

[a]Propylene refrigerant was available at −40, 0 and 40° F. Cooling water was available at 100° F.
[b]Steam was available at 239° F.

Table 18A summarizes the energy demand for each of the columns in the Examples. Energy demand is calculated using Table 18B which shows the number of BTUs which must be expended for each BTU of heat transferred in the process, for the various utilities available. As may be readily ascertained, operation at the optimal pressures (Example 1) or at the optimal pressures with a modified distillation sequence (Example 2) reduces energy demand to about 43% or 59%, respectively, of that of the conventional process (Comparative Example 1).

TABLE 18a

| | Tower | Split | Reflux | Feed | Reboiler |
|---|---|---|---|---|---|
| | | | Energy Demand ($10^6$ BTU ( ) /hr) | | |
| Comp. Ex. 1 | 11 | AB/CD | 54.6 | 0.8 | 30.8 |
| | 12 | A/B | 87.9 | 6.3 | 0.0 |
| | 13 | C/D | 0.3 | 0.2 | 66.3 |
| | ENERGY USE = 247.2 | | | | |
| Ex. 1 | 11 | AB/CD | 31.8 | 0.2 | 26.1 |
| | 12 | A/B | 22.2 | 0.4 | 0.6 |
| | 13 | C/D | 23.2 | 0.0 | 1.8 |
| | ENERGY USE = 106.3 | | | | |
| Ex. 2 | 14 | A/BCD | 48.0 | 0.1 | 53.9 |
| | 18 | B/CD | 5.4 | 0.1 | 13.8 |
| | 13 | C/D | 23.2 | 0.0 | 1.8 |
| | ENERGY USE = 146.3 | | | | |

TABLE 18B

| UTILITY | AVAILABLE T (° F.) | BTU (Expanded)[a] / BTU (Transferred) |
|---|---|---|
| Cooling Water | 75 | 0.046 |
| Propylene Refrigerant | 40 | 0.504 |
| | 0 | 1.321 |
| | −40 | 1.970 |
| Ethylene Refrigerant | −75 | 2.458 |
| | −110 | 3.230 |
| | −140 | 4.054 |

TABLE 18B-continued

| UTILITY | AVAILABLE T (° F.) | BTU (Expanded)[a] / BTU (Transferred) |
|---|---|---|
| Steam | 239 | 1.5 |

[a]BTU's expended on a thermal basis in order to transfer one BTU of heat in the process.

Table 19 summarizes the capital investment and annual utilities costs for each of the Examples. As may be readily ascertained, operation at the optimal pressures for Example 1 results in an estimated 43% increase in capital requirements, but reduces the utility costs by 53%. Example 2 is estimated to require 27% more capital investment than current practice, but reduces the utility costs by 42% per annum.

TABLE 19

| | Tower | Split | Capital Investment ($1000) | Annual Utility Cost ($1000) |
|---|---|---|---|---|
| Comp. Ex. 1 | 11 | AB/CD | 1287 | 3637 |
| | 12 | A/B | 2166 | 4435 |
| | 13 | C/D | 2617 | 2141 |
| | TOTALS | 6070 | 10213 | |
| Ex. 1 | 11 | AB/CD | 1519 | 2376 |
| | 12 | A/B | 3878 | 1194 |
| | 13 | C/D | 3266 | 1192 |
| | TOTALS | 8663 | 4762 | |
| Ex. 2 | 14 | A/BCD | 3398 | 4057 |
| | 18 | B/CD | 1027 | 705 |
| | 13 | C/D | 3266 | 1192 |
| | TOTALS | 7691 | 5954 | |

I claim:

1. Method of optimizing the expense of the recovery of $C_2/C_3$ hydrocarbons from a fluid mixture through fractional distillation comprising operating a system of towers in which each tower receives a single feed and produces two effluents and maintaining the pressure of each tower within ±15 psia of the pressure calculated from formulae:

$$\log_e (P^*) = 2.677 - \frac{309.4}{T_{FB}} + \frac{1147.6}{T_{\phi B}} + \frac{1087.4}{T_{BD}}$$

wherein:
P* = the pressure of each tower in psia
$T_{FB}$ = tower feed mixture bubble point temperature (° R) evaluated at 485 psia
$T_{\phi B}$ = tower overhead product mixture bubble point temperature (° R) evaluated at 485 psia
$T_{BD}$ = tower bottom product mixture dew point temperature (° R) evaluated at 485 psia.

* * * * *